United States Patent [19]

Bugaut et al.

[11] 4,125,367

[45] Nov. 14, 1978

[54] METAPHENYLENEDIAMINES AND DYEING COMPOSITIONS CONTAINING THE SAME

[75] Inventors: Andrée Bugaut, Boulogne; Jean-Jacques Vandenbossche, Aulnay, both of France

[73] Assignee: L'Oreal, Paris, France

[21] Appl. No.: 722,819

[22] Filed: Sep. 13, 1976

[30] Foreign Application Priority Data

Aug. 20, 1976 [FR] France .................. 76 25387

[51] Int. Cl.² .................. D06P 1/32; D06P 3/06; A61K 7/12
[52] U.S. Cl. .................. 8/11; 8/10.2; 260/578
[58] Field of Search .................. 8/11, 10.2

[56] References Cited

U.S. PATENT DOCUMENTS

3,037,057  5/1962  Tinsley et al. .................. 260/578

FOREIGN PATENT DOCUMENTS

2,549,451  5/1976  Fed. Rep. of Germany.
707,618  4/1954  United Kingdom.
1,012,793  12/1965  United Kingdom.

OTHER PUBLICATIONS

J. F. Corbett, "Hair Dyes" in Venkataraman's The Chemistry of Synthetic Dyes, vol. V (Academic Press, 1971), pp. 475-495.
"Coal Tar Hair Dyes" in *The Washington Post,* Dec. 15, 1977.
Amery, G. W. and Corbett, J. F., *J. Chem. Soc. (C),* 1967, pp. 1053-1057.

*Primary Examiner*—A. Lionel Clingman

*Attorney, Agent, or Firm*—Brisebois & Kruger

[57] ABSTRACT

A coupler having the general formula (I):

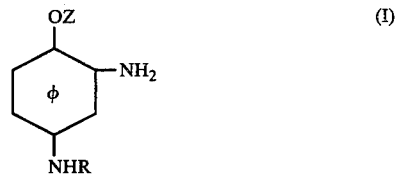

in which R is selected from the group consisting of hydrogen, alkyl or hydroxyalkyl having 1 to 3 carbon atoms, and in which Z is selected from the group consisting of hydroxyalkyl, alkoxyalkyl in which the alkoxy group comprises 1 to 2 carbon atoms, mesylaminoalkyl, acetylaminoalkyl, ureidoaminoalkyl or carbethoxyaminoalkyl, the alkyl groups constituting Z comprising from 2 to 3 carbon atoms, or the salts of the corresponding acids.

This coupler forms a dyeing composition when mixed with an oxidation base consisting of a paraphenylenediamine having the general formula:

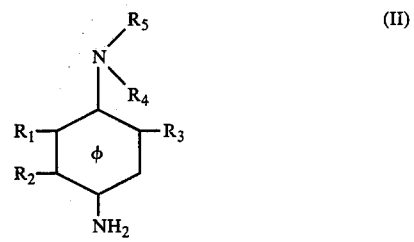

32 Claims, No Drawings

METAPHENYLENEDIAMINES AND DYEING COMPOSITIONS CONTAINING THE SAME

In the field of dyeing keratinic fibers, hair and furs, the metaphenylenediamines play an important role which has been known for a long time. They form part of the class of compounds currently called "couplers." The couplers, in association with the paraphenylenediamines or the paraaminophenols—compounds called oxidation bases—give rise in an alkaline oxidizing atmosphere to colored indamines, indoanilines or indophenols.

The association of the metaphenylenediamines with the paraphenylenediamines in an oxidizing alkaline atmosphere and in particular in the presence of hydrogen peroxide, gives rise to indamines capable of imparting to keratinic fibers, very strong blue colors.

Moreover, the metaphenylenediamines associated with the paraaminophenols give, in an oxidizing alkaline atmosphere, indoanilines, which impart to keratinic fibers more or less purple red colorations.

The metaphenylenediamines thus play, when considered as couplers, a double role in capillary dyeing: Contribution of blue and red, that is to say contribution of two fundamental colors which are indispensable to obtain not only blacks and greys, but also burnt or copper chestnuts.

Despite its important role this category of couplers is presently limited in practice to a very limited number of compounds. This excessively limited number of usable dyes is explained by the fact that one may only use dye compounds which are innocuousness, and color stable. It is thus that metatoluylene diamine is not used for reasons of non-innocuousness; and the 1-methyl-2-amino-N-methyl-4-amino benzene, 2-amino-N-methyl-4-amino anisole, 2-amino-4-amino-N-methyl anisole, 2-amino-N-$\beta$-hydroxyethyl 4-amino anisole, 1-methyl-2-amino-N-$\beta$-hydroxyethyl-4-amino benzene lead to shades which are unstable over a time, both in darkness and in the light. This instability is due principally to the ready cyclization into azinic molecules of the indoamines or indoanilines formed in situ during the oxidation dyeing, the azines formed then undergoing rapid photochemical degradation in the light.

The present invention describes new chemical compounds capable of constituting metaphenylenediamine couplers usable in hair dyeing compositions. The compounds according to the invention are particularly usable in capillary dyeing because they combine a very good innocuousness with the dyeing qualities of a good coupler.

The present invention produces, the new chemical compound of the general formula (I):

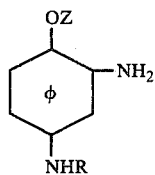

in which R represents a hydrogen atom, an alkyl or hydroxyalkyl radical having 1 to 3 carbon atoms, and in which Z represents a hydroxyalkyl radical, an alkoxyalkyl radical in which the alkoxy group comprises 1 to 2 carbon atoms, a mesylaminoalkyl radical, an acetyl aminoalkyl radical, a ureidoaminoalkyl radical or a carbethoxyaminoalkyl radical, the alkyl groups in the radicals making up Z comprising 2 to 3 atoms of carbon, or the corresponding acid salts.

The present invention produces a new dyeing composition for keratinic fibers and in particular for hair, said composition containing, in aqueous solution, at least one oxidation base which contains as a coupler, at least one compound of formula (I).

With the greater part of the paraphenylenediamines, in an alkaline oxidizing medium, the compounds of formula (I) impart to the hair strong blue colorations, more or less rich in green or in purple, resistant to the light, to bad weather, and to shampooing.

In a general way, in the dyeing composition according to the invention one may use as oxidation bases and paraphenylenediamines of the general formula (II):

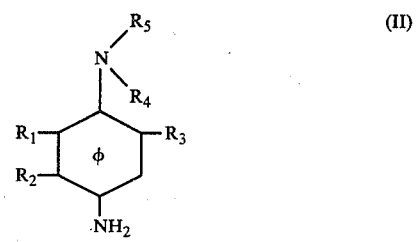

Or the corresponding acid salts; in which $R_1$, $R_2$ and $R_3$ are identical or different and represent a hydrogen atom, an alkyl radical having 1 to 2 carbon atoms or an alkoxy radical having 1 to 2 carbon atoms, $R_4$ and $R_5$ are identical or different and represent a hydrogen atom, an alkyl radical, hydroxyalkyl, alkoxyalkyl, in which the alkoxy group comprises 1 to 2 carbon atoms, carbamylalkyl, mesylaminoalkyl, acetylaminoalkyl, ureidoaminoalkyl, carbethoxyaminoalkyl, the alkyl groups in $R_4$ and $R_5$ having 1 to 3 carbon atoms, with the reservation that $R_1$ or $R_3$ represent hydrogen when $R_4$ and $R_5$ do not represent a hydrogen atom.

It should be noted however that the paraphenylenediamines have a chlorine or fluorine atom on the ring yielding with the compounds (I) violet colorations, which rapidly lose their chromaticity in the light. This is the case, for example, with 3-chloro-4-amino-N-$\beta$-hydroxyethyl aniline or 3-fluoro-4-amino-N-$\beta$-hydroxyethyl aniline.

To illustrate the invention one will hereafter describe by way of purely illustrative and non-limiting examples, the preparation and use of compounds of formula (I) as follows:

1. Dihydrochloride of (2,4-diamino) phenoxyethanol.
2. Dihydrochloride of (2-amino 4-amino-N-methyl)-phenoxyethanol.
3. Dihydrochloride of (2,4-diamino) phenylmethoxyethylether.
4. Dihydrochloride of (2,4-diamino) phenylmesylaminoethylether.

These four compounds give, in particular, blue colorations of very good stability with the following oxidation bases: paraphenylenediamine, paratoluylenediamine, 2-methyl 5-methoxy paraphenylenediamine, 2,6-dimethyl-3-methoxy paraphenylenediamine, 2,6-dimethyl paraphenylenediamine, 4-amino-N-methoxyethyl aniline, 4-amino-N,N-ethyl-carbamylmethyl aniline and 4-amino-N,N-di-$\beta$-hydroxyethyl aniline.

A certain number of compounds of formula (I) offer from the dyeing point of view, the supplemental advantage of being able to also give stable reds when they are associated with paraaminophenol or 2-methyl-4-amino phenol. This is the case with the two first compounds described as examples. The dyeing compositions containing these compounds may then contain at the same time paraphenylene diamines and paraaminophenols.

For the other compounds (I) which do not offer this supplementary advantage, one may in order to provide the red and violet necessary to the formulation of a capillary dyeing composition, add to the dyeing compositions containing them in addition to the paraphenylenediamines of formula (II) on the one hand leuco derivatives of indoanilines or indophenols such as: the 4,4'-dihydroxy-2-amino-5-methyl diphenylamine, 4,4'-dihydroxy-2-amino-N-β-hydroxyethyl-5-methyl-2'-chloro diphenylamine, 2,4'-diamino-4-hydroxy-5-methyl diphenylamine and on the other hand direct dyes such as, for example, 3-nitro-4-amino-N-β-hydroxyethyl anisole, (3-nitro 4-amino) phenoxyethanol, 3-nitro-4-amino-N-β-hydroxyethyl phenol, 2-β-hydroxyethyl-amino-5-nitro anisole.

The dyeing compositions constituting the object of the invention may also contain in addition to the coupler or couplers of the formula (I) and the oxidation base or bases associated therewith, the following products taken singly or in combination:

1. Other known couplers, for example, resorcin, metaaminophenol, 2-methyl-5-amino phenol, 5-amino-N-methyl-N-β-hydroxyethyl phenol, 6-hydroxy benzomorpholine, 2,6-dimethyl-5-acetylamino phenol, 2-methyl-5-carbethoxyamino phenol, 2-methoxy-5-carbethoxyamino phenol, 2-methyl-5-ureido phenol;

2. Polyaminophenols, monoaminodiphenols, diaminodiphenols, polyphenols such as trihydroxybenzene;

3. Leucoderivatives of indoaniline or indophenols;

4. Direct dyes and preferably nitrated dyes of the benzene series such as 1-amino-N,N-dihydroxyethyl-3-nitro-4-amino-N'-methyl benzene, 1-amino-N,N-methyl-β-hydroxyethyl-3-nitro-4-amino-N'-β-hydroxyethyl benzene, 1-amino-N,N-methyl-β-hydroxyethyl-3-nitro-4-amino-N'-methyl benzene, 3-nitro-4-amino-N-β-hydroxyethyl anisole, 3-nitro-4-amino-N-β-hydroxyethyl phenol, (3-nitro-4-amino) phenoxyethanol, (3-nitro-4-amino-N-methyl) phenoxyethanol, 2-amino-β-hydroxyethyl-5-nitro anisole;

5. Various usual additives such as penetrating agents, foaming agents, thickening agents, anti-oxidizing agents, alkalizing agents, perfumes, sequestrating agents, and film forming products.

The pH of the dyeing compositions according to the invention is a basic pH, for example, between 8 and 11.5. One prefers a pH between 9 and 10. Among the alkalizing agents which may be used, one may mention ammonia, the alkyl amines such as ethylamine or triethylamine, the alkanolamines such as the mono, di, and tri-ethanolamine, the ammonium derivatives, the hydroxides of sodium or potassium, and the carbonates of sodium or potassium.

One may also add to the composition according to the invention hydrosoluble anionic, cationic, non-ionic, or amphoteric surface-active agents. Among the surface active agents particularly useful one may mention the alkyl benzene sulfonates, the alkylnaphthalene sulfonates, the sulfates, ether sulfates and sulfonates of fatty alcohols, quaternary ammonium salts, such as triethyl cetylammonium bromide, cetyl pyridinium bromide, the diethanolamides of fatty acids, the acids and the polyoxyethylenated alcohols and the polyoxyethylenated alkylphenols. Preferably, the surface active agents are present in the composition according to the invention in a proportion between 0.5 and 30% by weight, and preferably between 4 and 25% by weight.

One may also add to the composition according to the invention organic solvents to solubilize the compounds which are not sufficiently soluble in water. Among the solvents which may advantageously be used one may mention by way of example ethanol, isopropanol, glycerin, glycols like butyl glycol, ethylene glycol, propylene glycol, monoethylether, and monomethylether of diethylene glycol and analogous products. The solvents may advantageously be present in the composition in a proportion running from 1 to 40% by weight and preferably between 5 and 30% by weight.

The thickening products which may be added into the compositon according to the invention may advantageously be taken from the group formed by sodium alginate, gum arabic, cellulose derivatives such as methylcellulose, hydroxyethylcellulose, hydroxypropyl methylcellulose, the sodium salt of carboxymethylcellulose, and the polymers of acrylic acid. One may also use mineral thickening agents such as bentonite. Preferably the thickening agents are present in a proportion between 0.5 and 5% by weight in proportion to the total composition and preferably between 0.5 and 3% by weight.

The antioxidizing agents which one may add to the composition according to the invention may be taken from the group formed by sodium sulfite, thioglycolic acid, and the acid sulfite of sodium, ascorbic acid, and hydroquinone. The antioxidizing agents may be present in the composition in a proportion comprising between 0.05 and 1% by weight in proportion to the total weight of the composition.

The dyeing composition according to the invention may contain oxidizing agents such as hydrogen peroxide, urea peroxide, or the persalts such as ammonium persulfate.

In a general way, the amount of the compounds of formula (I) present in the dyeing composition according to the invention is between 0.01 and 2.5% by weight in proportion to the total weight of the composition.

The dyeing composition according to the invention may be in the form of a liquid solution, a paste, a cream or gel, or any other appropriate form for bringing about a dyeing of keratinic fibers.

The compounds of formulas (I) may be easily prepared from compounds described in the previous applications by applicant (French Pat. Nos. 74 36651 filed Nov. 5, 1974, and 76 12985 filed Apr. 30, 1976). Beginning with these benzene compounds nitrated in the meta position with respect to the amine group, it suffices to bring about a reduction to transform the nitro group into an amine group and, possibly, then effectuate the acid hydrolysis in the case in which the starting products comprises an acetylated amine function.

In order that the object of the invention may be better understood, one will now describe by way of purely illustrative and non-limiting examples, the preparation of four compounds of formula (I) and the use of these compounds in dyeing compositions according to the invention:

EXAMPLE 1

Preparation of dihydrochloride of (2,4-diamino) phenoxyethanol.

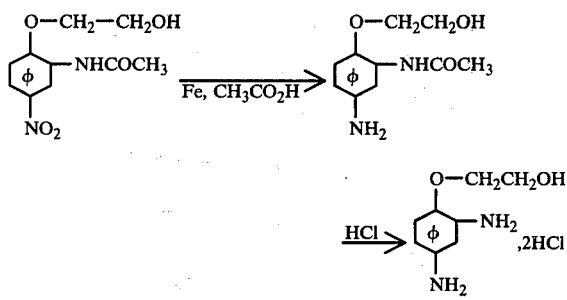

The starting compound is described in the second step of Example 6 of French Application No. 74-36651 filed Nov. 5, 1974, in the name of the applicant.

First step: Preparation of (2-acetylamino-4-amino) phenoxyethanol.

To 400 ml of water to which 6 ml of acetic acid has been added and which has been previously heated to 80° C., one adds 25 g of powdered iron and, little by little, under agitation, 0.16 mol (38.5 g) of (2-acetylamino-4-nitro) phenoxyethanol. After the additions, one keeps the reaction medium boiling in the water bath for 30 minutes. After neutralization with sodium carbonate it is filtered while boiling, the filtrate is cooled and then one precipitates by salting out by adding sodium chloride, (2-acetylamino 4-amino) phenoxyethanol. The expected product is drained, washed with very little ice water, and vacuum dried. It melts at 145° C.

Second step:
Preparation of dihydrochloride of (2,4-diamino) phenoxyethanol.

In 20 ml of hydrochloric acid at 36%, one dissolves 0.033 mols (7 g) of (2-acetylamino 4-amino) phenoxyethanol. One heats for two hours to reflux. After cooling, one drains the expected dihydrochloride which has precipitated. The product is drained, washed with a little hydrochloric acid and vacuum dried. It melts with decomposition at 225° C. Analysis gives the following results:

|   | Calculated for $C_8H_{14}N_2Cl_2O_2$ | Found |
|---|---|---|
| C % | 39.83 | 39.64 |
| H % | 5.80 | 5.72 |
| N % | 11.61 | 11.58 |
| Cl% | 29.46 | 29.51 |

EXAMPLE 2

Preparation of dihydrochloride of (2-amino 4-N-methylamino) phenoxyethanol

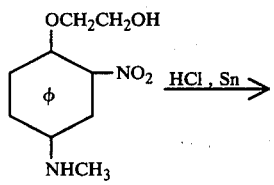

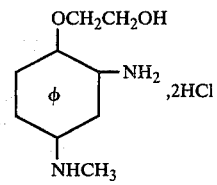

The starting compound is described in Example 5 of French Pat. No. 74-36651 above mentioned.

In 60 ml of hydrochloric acid (density = 1.19 at 75° C.) one adds simultaneously, little by little, under agitation 0.05 mols (10.6 g) of (2-nitro 4-amino-N-methyl) phenoxyethanol and 14.3 g of tin powder. After completion of the additions, one continues the agitation for 15 minutes at 90° C. The reaction mixture is drained hot. Filtrate is evaporated until dry under a vacuum. The residue is dissolved in 300 ml of water and the tin is precipitated in the form of the sulfide by bubbling with hydrogen sulfide. It is filtered. The filtrate is concentrated to 15 ml under a vacuum. The concentrated solution is cooled to −10° C. The dihydrochloride of the expected product crystallizes. It is drained, washed with very little ice water and then vacuum dried. It melts with decomposition at 225° C. The analysis of the product gives the following results:

|   | Calculated for $C_9H_{16}N_2O_2Cl_2$ | Found |
|---|---|---|
| C % | 42.35 | 42.08 |
| H % | 6.27 | 6.45 |
| N % | 10.98 | 10.77 |
| Cl% | 27.84 | 27.73 |

EXAMPLE 3

Preparation of dihydrochloride of (2,4-diamino) phenyl-β-methoxyethylether.

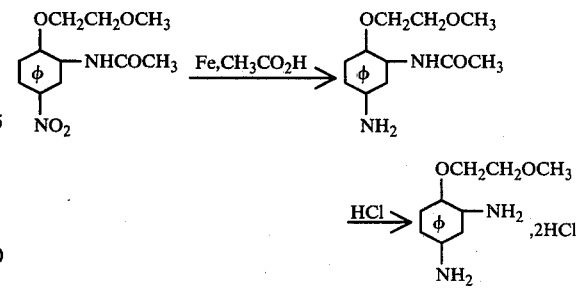

First step:
Preparation of (2-acetylamino 4-amino) phenyl β-methoxyethylether.

To 100 ml of water to which 4 ml of acetic acid has been added and which has already been heated to 90° C., one adds 13 g of powdered iron and, little by little, under agitation, 0.078 mol (20 g) of 2-acetylamino-4-nitro) phenyl-β-methoxy-ethylether (product described in the first step of Example 8 of French Pat. No. 76-12985 filed Apr. 30, 1976, in the name of the applicant). The addition being terminated, one maintains the reaction mixture in the boiling water bath for 30 minutes. It is filtered hot. After the addition of sodium chloride to the filtrate, the expected product precipitates by salting out. It is drained, washed with very little ice water. It melts at 130° C.

Second step:
Preparation of dihydrochloride of (2,4-diamino) phenyl-β-methoxyethylether.

0.067 mol (15 g) of 2-acetylamino 4-amino) phenyl-β-methoxyethylether is introduced into 30 ml of 36% hydrochloric acid. One heats 30 minutes in the boiling water bath. After cooling the dihydrochloride of the expected product crystallizes. It is drained, recrystalized in alcohol, and vacuum dried. The product melts with decomposition at 215° C.

The analysis gives the following results:

|  | Calculated for $C_9H_{16}N_2O_2Cl_2$ | Found |
|---|---|---|
| C % | 42.35 | 42.47 |
| H % | 6.27 | 6.34 |
| N % | 10.98 | 10.85 |
| Cl% | 27.84 | 27.83 |

EXAMPLE 4

Preparation of dihydrochloride of (2,4-diamino) phenyl-mesylaminoethylether

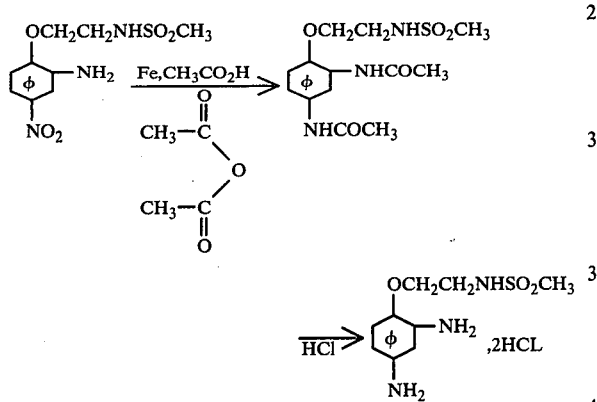

First step:
Preparation of (2,4-diacetylamino)-phenyl-mesylaminoethylether.

Into 20 ml of water to which 2 ml of acetic acid has been added and which has been brought to 90° C., one adds 3.5 g of powdered iron and, little by little, under agitation, 0.02 mol (5.5 g) of (4-nitro-6-amino) phenyl mesylaminoethylether (product described in Example 12 of French Pat. No. 76-12985 aforesaid). The reflux is maintained under agitation for 30 minutes. It is drained while boiling and the precipitate washed in boiling water. 6 ml of acetic anhydride is added to the filtrate and the reaction medium heated for several minutes in a boiling water bath. After cooling the expected product crystallizes. It is drained, washed with water, vacuum dried. It melts at 191° C.

Second step: Preparation of dihydrochloride of (2,4-diamino) phenyl-mesylaminoethylether.

One heats for 45 minutes in a boiling water bath 0.017 mol (5.6 g) of (2,4-diacetylamino) phenyl-mesylaminoethylether in 14 ml of hydrochloric acid at 36%. After cooling, the dihydrochloride of the expected product precipitates in crystallized form. The product is drained, recrystallized in alcohol and vacuum dried at 60° C.

Analysis gives the following results:

|  | Calculated for $C_9H_{17}N_3O_3S\ Cl_2$ | Found |
|---|---|---|
| C % | 33.96 | 33.93 |
| H % | 5.38 | 5.45 |
| N % | 13.20 | 13.12 |
| Cl% | 22.28 | 22.10 |
| S % | 10.08 | 10.15 |

EXAMPLE 5

The following dyeing composition is prepared:

| Compound of example 3 | 0.127 g |
|---|---|
| 4-amino-N-ethyl-N-carbamylmethyl aniline | 0.193 g |
| Butylglycol | 20 g |
| Lauric alcohol having 10.5 mols of ethylene oxide. | 8 g |
| Ammonia at 22° B | 4.5 g |
| Water, q.s. | 100 g |

The pH is 10.3.
At the moment of use one adds 35 g of hydrogen peroxide at 20 volumes. This mixture applied to 95% naturally white hair for 20 minutes at ambient temperature imparts thereto, after rinsing and shampooing, a sky blue coloration.

EXAMPLE 6

The following dyeing composition is prepared:

| Compound of example 1 | 0.120 g |
|---|---|
| Dihydrochloride of 2-methyl-5-methoxy paraphenylene diamine | 0.112 g |
| Alcohol at 96° | 20 g |
| Ammonia at 22° B | 5 g |
| Diethanolamides of fatty acids of copra | 7.5 g |
| Water, q.s. | 100 g |

The pH is equal to 10.
At the moment of use one adds 45 g of hydrogen peroxide at 20 volumes.
This mixture applied to 95% naturally white hair for 20 minutes at ambient temperature imparts thereto, after rinsing and shampooing, a blue turquoise coloration.

EXAMPLE 7

The following dyeing composition is prepared:

| Compound of example 4 | 0.016 g |
|---|---|
| Sulfate of 3-methyl-4-methoxyalkylamino aniline | 0.028 g |
| Carboxymethylcellulose | 5 g |
| Water, q.s. | 100 g |
| Ammonia at 22° B | 6 g |

The pH is equal to 11.
At the moment of use 15 g of hydrogen peroxide at 20 volumes is added.
This mixture applied for 25 minutes at 30° C. to bleached hair imparts thereto, after rinsing and shampooing, a sky blue coloration.

EXAMPLE 8

The following dyeing composition is prepared:

| Compound of example 1 | 0.362 g |
|---|---|
| Paraaminophenol | 0.218 g |
| Butylglycol | 5 g |
| Lauric alcohol oxyethylenated with 10.5 mols of ethylene oxide | 5 g |
| Ammonia at 22° B | 6 g |

| | |
|---|---|
| Water, q.s. | 100 g |

The pH is equal to 10.3.

At the moment of use 25 g of hydrogen peroxide at 20 volumes is added.

This mixture applied to 95% naturally white hair for 15 minutes at 25° C. imparts thereto, after rinsing and shampooing, a slightly purplish sombre red coloration.

EXAMPLE 9

The following dyeing composition is prepared:

| | |
|---|---|
| Compound of example 1 | 0.060 g |
| 4-amino-N,N-di-β-hydroxyethyl aniline sulfate | 0.059 g |
| Ammonium lauryl sulfate | 5 g |
| Ammonia at 22° B | 2 g |
| Water, q.s. | 100 g |

The pH is equal to 9.7.

10 g of hydrogen peroxide at 20 volumes is added at the moment of use.

This mixture applied for 15 minutes at 25° C. to bleached hair imparts thereto, after rinsing and shampooing, a clear silvered turquoise blue coloration.

EXAMPLE 10

The following dyeing composition is prepared:

| | |
|---|---|
| Compound of example 3 | 0.255 G |
| Dihydrochloride of 4-amino-N-methyl aniline | 0.195 g |
| Oleic alcohol oxyethylenated with 2 mols of ethylene oxide | 3 g |
| Oleic alcohol oxyethylenated with 4 mols of ethylene oxide | 4.4 g |
| Ammonia at 22° B | 6 g |
| Water, q.s. | 100 g |

The pH is equal to 10.

At the moment of use 25 g of hydrogen peroxide at 20 volumes is added.

This mixture applied for 10 minutes at 30° C. to 95% naturally white hair imparts thereto, after rinsing and shampooing, a royal blue coloration.

EXAMPLE 11

The following dyeing composition is prepared:

| | |
|---|---|
| Compound of example 1 | 0.241 g |
| 3-methyl-4-amino-N-methyl aniline sulfate | 0.187 g |
| Paraaminophenol | 0.109 g |
| 2-nitro-5-amino-N,N-diethyl phenol | 1 g |
| Propyleneglycol | 20 g |
| Nonylphenol having 4 mols of ethylene oxide | 8 g |
| Nonylphenyl having 9 mols of ethylene oxide | 8 g |
| Ammonia at 22° B | 7.5 g |
| Water, q.s. | 100 g |

The final pH is equal to 10.2.

At the moment of use 70 g of hydrogen peroxide at 20 volumes is added.

This mixture applied for 15 minutes at 30° C. to 95% naturally white hair imparts thereto, after rinsing and shampooing, a metallic blue gray coloration.

EXAMPLE 12

The following dyeing composition is prepared:

| | |
|---|---|
| Compound of example 1 | 2.5 g |
| Dihydrochloride of 2,6-dimethyl-5-methoxy paraphenylenediamine | 2.64 g |
| Monomethyl ester of diethyleneglycol | 8.8 g |
| Ammonia at 22 ° B | 12 g |
| Water, q.s. | 100 g |

The pH is equal to 9.5.

At the moment of use 100 g of hydrogen peroxide at 20 volumes is added.

This mixture applied for 15 minutes at 25° C. to bleached hair imparts thereto, after rinsing and shampooing, a clear green blue coloration.

EXAMPLE 13

The following dyeing composition is prepared:

| | |
|---|---|
| Compound of example 1 | 0.25 g |
| Resorcin | 0.2 g |
| 6-hydroxy phenomorpholine | 0.06 g |
| Paraaminophenol | 0.15 g |
| Dihydrochloride of 2-methyl-5-methoxy paraphenylenediamine | 0.05 g |
| Dihydrochloride of 2,5-diamino pyridine | 0.1 g |
| 3-nitro-4-amino-N-β-hydroxyethyl phenol | 0.175 g |
| 2-amino-N-δ-aminopropyl anthraquinone | 0.15 g |
| Monomethyl ether of diethyleneglycol | 10 g |
| Ammonia at 22° B | 5 g |
| Water, q.s. | 100 g |

The final pH is equal to 10.

At the moment of use 40 g of hydrogen peroxide at 20 volumes is added.

This mixture applied to bleached hair for 30 minutes at ambient temperature to imparts thereto, after rinsing and shampooing, a reddish copper maroon coloration.

EXAMPLE 14

The following dyeing composition is prepared:

| | |
|---|---|
| Compound of example 4 | 0.954 g |
| Dihydrochloride of 2,6-dimethyl-3-methoxy paraphenylenediamine | 1.43 g |
| Alkyl ammonium sulfate in $C_{12}$, $C_{14}$ (70% of $C_{12}$ and 30% of $C_{14}$) | 15 g |
| Lauric alcohol having 10.5 mols of ethylene oxide | 5 g |
| Ammonia at 22° B | 10 g |
| Water, q.s. | 100 g |

The final pH is equal to 10.2.

At the moment of use, 75 g of hydrogen peroxide at 20 volumes is added. This mixture applied for 20 minutes at 25° C. to 95% naturally white hair imparts there, after rinsing and shampooing, a clear pure blue coloration.

EXAMPLE 15

The following dyeing composition is prepared:

| | |
|---|---|
| Compound of example 1 | 0.106 g |
| Paraaminophenol | 0.3 g |
| Dihydrochloride of paratoluylenediamine | 1.7 g |
| Resorcin | 0.403 g |
| Metaaminophenol | 0.228 g |
| Alkyl ammonium sulfate in $C_{12}C_{14}$ (70% of $C_{12}$ and 30% of $C_{14}$) | 15 g |
| Lauric alcohol having 10.5 mols of ethylene oxide | 5 g |
| Ammonia at 22° B (d = 0.92) | 10 g |
| Water, q.s. | 100 g |

The final pH is equal to 10.4.

At the moment of use, 100 g of hydrogen peroxide at 20 volumes is added.

This composition applied for 20 minutes at 20° C. to 95% naturally white hair imparts thereto, after rinsing and shampooing, a black coloration.

EXAMPLE 16

The following dyeing composition is prepared:

| | |
|---|---|
| Compound of example 1 | 0.05 g |
| Dihydrochloride of paratoluylenediamine | 0.1 g |
| 4,4'-dihydroxy-2-amino-5-methyl diphenylamine | 0.265 g |
| 4,4'-dihydroxy-2-amino-N-$\beta$-hydroxyethyl-5-methyl-2'-chloro-diphenylamine | 0.35 g |
| Dihydrochloride of 2,6-diamino hydroquinone | 0.145 g |
| Trihydrochloride of 2,6-diamino-4-amino-N,N-diethyl phenol | 0.20 g |
| 3-nitro-4-amino-N-$\beta$-hydroxyethyl anisole | 0.35 g |
| Diethanolamides of fatty acids of copra | 7.6 g |
| Propyleneglycol | 20 g |
| Ammonia at 22° B | 6 g |
| Water, q.s. | 100 g |

The final pH is equal to 9.8.

At the moment of use 100 g of hydrogen peroxide at 20 volumes is added.

This mixture applied to bleached hair for 20 minutes at 25° C. imparts thereto, after rinsing and shampooing, a mahogany coloration.

EXAMPLE 17

The following dyeing composition is prepared:

| | |
|---|---|
| Compound of example 3 | 0.12 g |
| Trihydroxybenzene | 0.82 g |
| N-ethyl-4-amino-N-carbamylmethyl aniline | 2.6 g |
| 3-nitro-4-N-amino-$\beta$-hydroxyethyl phenol | 0.29 g |
| Alcohol at 96° | 20 g |
| Triethanolamine | 6 g |
| Water, q.s. | 100 g |

The pH is equal to 9.

At the moment of use 60 g of hydrogen peroxide at 20 volumes is added.

This mixture applied to bleached hair for 20 minutes at 20° C. imparts thereto, after rinsing and shampooing, a deep brown coloration having light violet glints.

EXAMPLE 18

The following dyeing composition is prepared:

| | |
|---|---|
| Compound of example 1 | 0.05 g |
| Trihydroxybenzene | 0.34 g |
| Dihydrochloride of 2,6-dimethyl paraphenylenediamine | 0.67 g |
| 3-nitro-4-amino-N-$\beta$-hydroxyethyl phenol | 0.2 g |
| Butylglycol | 4.8 g |
| Lauric alcohol oxyethylenated with 10.5 mols of ethylene oxide | 4.8 g |
| Triethanolamine | 4 g |
| Water, q.s. | 100 g |

The pH is equal to 8.

At the moment of use 50 g of hydrogen peroxide at 20 volumes is added.

This mixture applied for 25 minutes at 25° C. to bleached hair imparts thereto, after rinsing and shampooing, a burnt grey coloration.

EXAMPLE 19

The following dyeing composition is prepared:

| | |
|---|---|
| Compound of example 1 | 0.06 g |
| Resorcin | 0.26 g |
| Metaaminophenol | 0.29 g |
| Dihydrochloride of 2-methyl-4-amino phenol | 1 g |
| Dihydrochloride of 4-amino-N-methyl aniline | 0.315 g |
| 4-amino-methyl phenol sulfate | 0.11 g |
| 3-nitro-4-amino-N-$\beta$-hydroxyethyl anisole | 0.65 g |
| Alkyl ammonium sulfate in $C_{12}$, $C_{14}$ (70% of $C_{12}$ and 30% of $C_{14}$) | 15 g |
| Lauric alcohol having 10.5 mols of ethylene oxide | 5 g |
| Ammonia at 22° B | 10 g |
| Water, q.s. | 100 g |

The pH is equal to 10.3.

At the moment of use 100 g of hydrogen peroxide at 20 volumes is added.

This mixture applied for 20 minutes at 20° C. to 95% naturally white hair imparts thereto, after rinsing and shampooing, a copper coloration.

EXAMPLE 20

The following dyeing composition is prepared:

| | |
|---|---|
| Compound of example 3 | 0.2 g |
| Dihydrochloride of 2-methyl-5-methoxy paraphenylenediamine | 0.2 g |
| 4-amino-N,N-$\beta$-hydroxyethyl aniline sulfate | 0.2 g |
| Metaaminophenol | 0.3 g |
| 6-hydroxy benzomorpholine | 0.1 g |
| 3-nitro-4-amino-N-$\beta$-hydroxyethyl anisole | 0.2 g |
| 4-mino-N-methyl phenol sulfate | 0.4 g |
| Monomethyl ester of diethyleneglycol | 9 g |
| Ammonia at 22° B | 10 g |
| Water, q.s. | 100 g |

The pH is equal to 10.7.

At the moment of use 100 g of hydrogen peroxide at 20 volumes is added.

This mixture applied for 30 minutes at 20° C. to bleached hair imparts thereto, after rinsing and shampooing, a very deep reddish chestnut coloration.

EXAMPLE 21

The following dyeing composition is prepared:

| | |
|---|---|
| Compound of example 4 | 0.105 g |
| Resorcin | 15 g |
| Dihydrochloride of 2,6-dimethyl-5-methoxy paraphenylenediamine | 0.3 g |
| 1-phenyl-3-methyl pyrazolone | 0.1 g |
| 3-nitro-4-amino-N-$\beta$-hydroxyethyl phenol | 0.2 g |
| Hydrochloride of (2-amino-4-nitro) phenoxyethanol | 0.25 g |
| 4,4'-dihydroxy-2-amino-5-methyl diphenylamine | 0.4 g |
| Butylglycol | 15 g |
| Nonylphenol having 4 mols of ethylene oxide | 8 g |
| Nonylphenol having 9 mols of ethylene oxide | 9 g |
| Ammonia at 22° B | 5 g |
| Water, q.s. | 100 g |

The pH is equal to 9.8.

At the moment of use, 80 g of hydrogen peroxide at 20 volumes is added.

This mixture applied for 25 minutes at 20° C. to bleached hair imparts thereto, after rinsing and shampooing, a clear golden chestnut coloration.

EXAMPLE 22

The following dyeing composition is prepared:

| | |
|---|---|
| Compound of example 3 | 0.13 g |
| 3-fluoro-4-amino-N-hydroxyethyl aniline sulfate | 0.22 g |
| Trihydrochloride of 4-amino-N-diethyl-2,6-diamino phenol | 0.12 g |
| N[(4-hydroxy) phenyl]-2-methyl-5-amino benzoquinone imine | 0.70 g |
| Butylglycol | 5 g |
| Lauric alcohol oxyethylenated with 10.5 mols of ethylene oxide | 5 g |

| -continued | |
|---|---|
| Triethanolamine | 1.1 g |
| Water, q.s. | 100 g |

At the moment of use, 10 g of urea peroxide is added in 100 g of water.

This mixture applied for 25 minutes at 20° C. to bleached hair imparts thereto, after rinsing and shampooing, a burnt beige grey coloration.

EXAMPLE 23

The following dyeing composition is prepared:

| | | |
|---|---|---|
| Compound of example 4 | 0.075 | g |
| Compound of example 1 | 0.025 | g |
| Resorcin | 0.11 | g |
| m-amino phenol | 0.1 | g |
| 4-amino-N-phenol sulfate | 0.2 | g |
| 4-amino-N-β-methoxyethyl aniline sulfate | 0.3 | g |
| 3-nitro-4-amino phenoxyethanol | 0.3 | g |
| 2,4'-diamino-4-hydroxy-5-methyl diphenylamine | 0.25 | g |
| 2-amino-N-β-hydroxyethyl-5-nitro-anisole | 0.125 | g |
| Hydroquinone | 0.0325 | g |
| | 3.33 | g |
| $R \left( -OCH_2CH-\atop CH_2OH \right)_2 OH$ (R being an oleyl radical) | | |
| | 4.95 | g |
| $R \left( -OCH_2CH-\atop CH_2OH \right)_4 OH$ (R being an oleyl radical) | | |
| Propyleneglycol | 6.6 | g |
| Ammonia at 22° B | 10 | g |
| Water, q.s. | 100 | g |

The pH is equal to 10.3.

At the moment of use 75 g of hydrogen peroxide at 20 volumes is added.

This mixture applied for 20 minutes at ambient temperature to 95% naturally white hair imparts thereto, after rinsing and shampooing, a bronze coloration.

EXAMPLE 24

The following dyeing composition is prepared:

| | |
|---|---|
| Dye of example 2 | 0.14 g |
| Dihydrochloride of 2,6-dimethyl-3-methoxy paraphenylenediamine | 0.20 g |
| Trihydrochloride of 4-amino-N-diethyl-2,6-diamino phenol | 0.1 g |
| N[(4-hydroxy) phenyl]2-methyl-5-amino benzoquinone imine | 0.5 g |
| Butylglycol | 5 g |
| Lauric alcohol oxyethylenated with 10.5 mols of ethylene oxide | 5 g |
| Triethanolamine | 1.1 g |
| Water, q.s. | 100 g |

The pH is equal to 8.

10 g of urea peroxide in solution in 100 g of water is added at the moment of use.

This solution applied for 20 minutes at ambient temperature to bleached hair imparts thereto, after rinsing and shampooing, a deep grey coloration.

EXAMPLE 25

The following dyeing composition is prepared:

| | |
|---|---|
| Compound of example 2 | 0.20 g |
| Paraaminophenol | 0.60 g |
| 4-amino-N-β-methoxyethyl aniline sulfate | 0.325 g |
| Metaaminophenol | 0.44 g |
| (3-nitro-4-amino) phenoxyethanol | 0.25 g |
| Butylglycol | 20 g |
| Diethanolamides of fatty acids of copra | 7.4 g |
| Ammonia at 22° B | 6 g |

| -continued | |
|---|---|
| Water, q.s. | 100 g |

The pH is equal to 10.5.

At the moment of use 100 g of hydrogen peroxide at 20 volumes is added. This dyeing composition applied for 20 minutes at 25° C. to 95% naturally white hair imparts thereto, after rinsing and shampooing, a golden chestnut coloration.

EXAMPLE 26

The following dyeing composition is prepared:

| | |
|---|---|
| Compound of example 3 | 0.0012 g |
| 4-amino-N-β-methoxyethyl aniline sulfate | 0.00125 g |
| Butylglycol | 7.5 g |
| Product sold under the commercial name of "Carbopol 934" | 3.37 g |
| Polymer of acrylic acid (M.W. = 2 - 3 millions) manufactured by the Goodrich Chemical Co. | |
| Ammonia to 22° B | 7.5 g |
| Water, q.s. | 100 g |

The pH is equal to 8.

At the moment of use, 15 g of hydrogen peroxide at 20 volumes is added. This composition applied for 30 minutes at 25° C. to bleached hair imparts thereto, after rinsing and shampooing, a clear blue coloration.

It is well understood that the modes of preparation and examples of composition given hereinabove are in no way limitative and may give place to all desirable modifications without thereby departing from the scope of the invention.

We claim:

1. A dyeing composition for keratinic fibers and human hair, said composition containing in aqueous solution a dyeing amount of at least 1 oxidation base that contains as a coupler, at least 1 compound according to having the general formula (I):

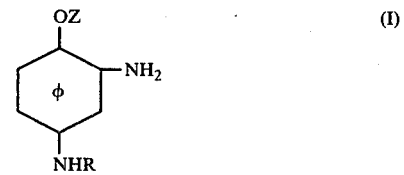

in which R is selected from the group consisting of hydrogen, alkyl or hydroxyalkyl having 1 to 3 carbon atoms, and in which Z is selected from the group consisting of hydroxyalkyl, alkoxyalkyl in which the alkoxy group comprises 1 to 2 carbon atoms, mesylaminoalkyl, acetylaminoalkyl, ureidoaminoalkyl or carbethoxyaminoalkyl, the alkyl groups constituting Z comprising from 2 to 3 carbon atoms, or the salts of the corresponding acids.

2. The composition of claim 1 which contains as a coupler the compound in which R is H and Z is hydroxyethyl.

3. The composition of claim 1 which contains as a coupler, the compound in which R is methyl and Z is hydroxyethyl.

4. The composition of claim 1 which contains as a coupler, the compound in which R is H and Z is methoxyethyl.

5. The composition of claim 1 which contains as a coupler, the compound in which R is H and Z is mesylaminoethyl.

6. Composition according to claim 1 characterized by the fact that it contains as oxidation base at least one paraphenylenediamine of the general formula (II):

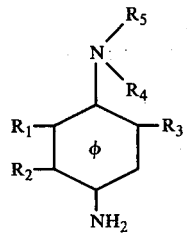

or the corresponding acid salts; in which $R_1$, $R_2$, $R_3$ are identical or different and represent hydrogen, alkyl, or alkoxy having 1 to 2 carbon atoms, $R_4$ and $R_5$ are identical or different and represent hydrogen, alkyl, hydroxyalkyl, alkoxyalkyl in which the alkoxy group comprises 1 to 2 atoms of carbon, carbamylalkyl, mesylaminoalkyl, acetylaminoalkyl, ureidoaminoalkyl, carbethoxyaminoalkyl, the alkyl groups $R_4$ and $R_5$ having 1 to 3 carbon atoms, with the reservation that when $R_1$ and $R_3$ represent hydrogen when $R_4$, $R_5$ do not represent hydrogen.

7. Composition according to claim 2 which contains as the oxidation base, a base selected from the group consisting of paraphenylenediamine, paratoluylenediamine, 2-methyl-5-methoxy paraphenylenediamine, 2,6-dimethyl paraphenylenediamine, 2,6-dimethyl-3-methoxy paraphenylenediamine, 4-amino-N-methoxyethyl aniline, 4-amino-N,N-ethyl-carbamylmethyl aniline, and 4-amino-N-N,di-β-hydroxyethyl aniline.

8. Composition according to claim 2 which contains as the oxidation base paraaminophenol or 2-methyl-4-amino phenol.

9. Composition according to claim 1 which contains on the one hand leucoderivatives of indoanilines or indophenols such as 4,4'-dihydroxy-2-amino-5-methyl diphenylamine, 4,4'-dihydroxy-2-amino-N-β-hydroxyethyl-5-methyl-2'-chloro diphenylamine, 2,4'-diamino-4-hydroxy-5-methyl diphenylamine and on the other hand direct dyes such for example as 3-nitro-4-amino-N-β-hydroxyethyl anisole, (3-nitro-4-amino) phenoxyethanol, 3-nitro-4-amino-N-β-hydroxyethyl phenol, 2-amino-β-hydroxyethyl-5-nitro-anisole.

10. Composition according to claim 1 which contains at least one coupler other than those of formula (I).

11. Composition according to claim 10 in which the other coupler or couplers than those of formula (I) is or are selected from the group consisting of resorcin, metaaminophenol, 2-methyl-5-amino phenol, 5-amino-N-methyl-N-β-hydroxyethyl phenol, 6-hydroxy benzomorpholine, 2,6-dimethyl-5-acetylamino phenol, 2-methyl-5-carbethoxyamino phenol, 2-methoxy-5-carbethoxyamino phenol and 2-methyl-5-ureido phenol.

12. Composition according to claim 1, which contains at least one compound taken in the group formed by polyaminophenols, monoaminodiphenols, diaminodiphenols, polyphenols.

13. Composition according to claim 1, which contains at least one direct dye.

14. Composition according to claim 13 in which the correct dye or dyes is or are taken in the group formed by the nitrated dyes of the benzene series.

15. Composition according to claim 14 in which the nitrated dye or dyes of the benzene series is or are taken from the group consisting of 1-amino-N,N-dihydroethyl-3-nitro-4-amino-N'-methyl benzene, the 1-amino-N,N-methyl-β-hydroxyethyl-3-nitro-4-amino-N'-hydroxyethyl benzene, 1-amino-N,N-methyl-β-hydroxyethyl-3-nitro-4-amino-N'-methyl benzene, 3-nitro-4-amino-N-β-hydroxyethyl anisole, 3-nitro-4-amino-N-β-hydroxyethyl phenol, (3-nitro 4-amino) phenoxyethanol, (3-nitro-4-amino-N-methyl) phenoxyethanol and 2-β-hydroxyethylamino-5-nitro anisole.

16. Composition according to claim 1, which contains at least one additive taken in the group formed by the penetrating agents, the foaming agents, the thickening agents, the anti-oxidizing agents, the alkalizing agents, the perfumes, the sequestrating agents, and the film forming products.

17. Composition according to claim 1, having a pH between 8 and 11.5 and preferably between 9 and 10.

18. Composition according to claim 17 in which the alkalyzing agents are selected from the group consisting of ammonia, the alkylamines, the alkanolamines, the ammonium derivatives, the hydroxides of sodium or potassium, the carbonates of sodium or potassium.

19. Composition according to claim 1 which contains when about to be applied to the hair at least one oxidizing agent such as hydrogen peroxide, urea peroxide, or persalts such as the persulfate of ammonium.

20. Composition according to claim 1 which contains at least one hydrosoluble surface active agent.

21. Composition according to claim 20, in which the hydrosoluble surface active agent is selected from the group consisting of alkylbenzene-sulfonates, the alkylnaphthalene-sulfonates, the sulfates, ether sulfates and sulfonates of fatty alcohols, the quaternary ammonium salts such as trimethyl cetylammonium bromide, cetyl pyridinium bromide, the diethanolamides of fatty acids, the polyoxyethylenated acids and alcohols, and the polyoxyethylenated alkylphenols.

22. Composition according to claim 20 which contains 0.5 to 30% by weight of surface-active agents in proportion to the total composition.

23. Composition according to claim 1 which contains at least one organic solvent.

24. Composition according to claim 23 in which the organic solvent is selected from the group consisting of ethanol, isopropanol, glycerin, glycols such as ethylene glycol, propylene glycol, the monoethylether and monomethylether of diethylene glycol.

25. Composition according to claim 23 which contains 1 to 40% by weight of organic solvent in proportion to the total weight of the composition.

26. Composition according to claim 1 which contains at least one thickening product.

27. Composition according to claim 26 in which the thickening product is selected from the group consisting of sodium alginate, gum arabic, the derivatives of cellulose such as methylcellulose, hydroxyethylcellulose, hydroxypropylmethylcellulose, the sodium salt of carboxymethylcellulose, the polymers of acrylic acid and bentonite.

28. Composition according to claim 26 which contains 0.5 to 5% by weight of thickening agent in proportion to the total weight of the composition.

29. Composition according to claim 1 which contains at least one anti-oxidizing agent.

30. Composition according to claim 29 in which the anti-oxidizing agent is selected from the group consisting of sodium sulfite, thioglycolic acid, sodium acid sulfite, ascorbic acid and hydroquinone.

31. Composition according to claim 29 which contains 0.05 to 1% by weight of anti-oxidizing agent in proportion to the total weight of the composition.

32. Composition according to claim 1 which contains 0.01–2.5% by weight of at least one compound of formula (I).

* * * * *